US006702116B2

(12) United States Patent
Hummel

(10) Patent No.: US 6,702,116 B2
(45) Date of Patent: Mar. 9, 2004

(54) PERSONAL HYGIENE PRODUCT DISPOSAL CONTAINER

(76) Inventor: Emily K. Hummel, 370 Parkside Dr., Sycamore, IL (US) 60178

( * ) Notice: Subject to any disclaimer, the term of this patent is extended or adjusted under 35 U.S.C. 154(b) by 85 days.

(21) Appl. No.: 10/044,872

(22) Filed: Jan. 10, 2002

(65) Prior Publication Data

US 2003/0127343 A1 Jul. 10, 2003

(51) Int. Cl.[7] ................................................ A61B 17/06
(52) U.S. Cl. ....................................... 206/438; 206/204
(58) Field of Search ................................ 206/204, 210, 206/438, 223, 38, 440, 581, 823, 812; 604/385.02–385.05; 229/68.1, 72, 75

(56) References Cited

U.S. PATENT DOCUMENTS 3,062,371 A * 11/1962 Beltle ......................... 206/440
3,617,311 A * 11/1971 Beltle et al. .................. 426/86
3,683,987 A * 8/1972 Robertson .................... 383/99
4,312,085 A 1/1982 Potter
4,402,689 A 9/1983 Baum
4,502,599 A * 3/1985 Perecman ................... 206/554
4,581,027 A 4/1986 Alvarado
4,692,162 A * 9/1987 Binker et al. .......... 604/385.13
4,765,477 A 8/1988 Fröïdh et al.
4,781,712 A 11/1988 Barabino et al.
4,838,327 A * 6/1989 Ambler et al. .............. 141/114
4,846,828 A 7/1989 Mendelsohn
4,857,066 A 8/1989 Allison
5,121,864 A * 6/1992 Geschwind ................. 224/230
5,261,531 A 11/1993 Nieves
H1363 H 10/1994 Leeker
5,474,818 A * 12/1995 Ulrich et al. .............. 428/34.3
5,484,636 A 1/1996 Berg, Jr. et al.
5,569,228 A 10/1996 Byrd et al.
5,884,771 A * 3/1999 McCormick ................ 206/581
5,950,818 A 9/1999 Paulsen
6,036,679 A * 3/2000 Balzar et al. ............... 604/387
6,039,175 A * 3/2000 Wright ........................ 206/37
6,059,100 A 5/2000 Jones
6,183,456 B1 * 2/2001 Brown et al. .......... 604/385.01
6,186,993 B1 * 2/2001 Toyoshima et al. .... 604/385.02

* cited by examiner

*Primary Examiner*—Shian Luong
(74) *Attorney, Agent, or Firm*—Marshall, Gerstein & Borun LLP

(57) ABSTRACT

A container and a method of assembling a container which cleanly and conveniently disposes of used feminine products. The container is manufactured from a sheet, normally of paper treated to be water resistant. It is folded and sealed about itself to form a triangular container, with a wide opening along one side. The opening is sealed with a releasable sealing agent. Once used, the container can then be folded into a small, convenient package which can easily be carried in a purse, and disposed of at the user's convenience.

15 Claims, 7 Drawing Sheets

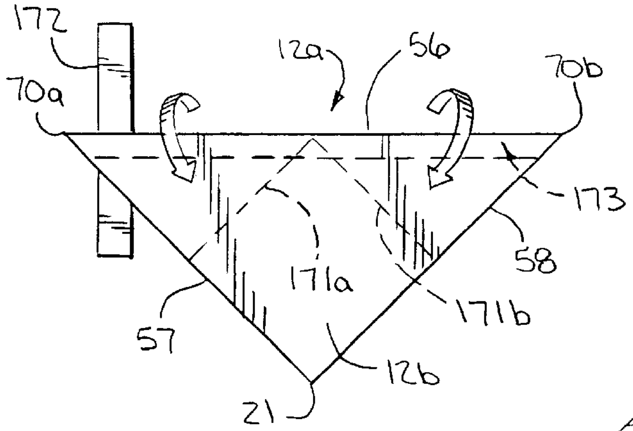
FIG. 17
FIG. 18
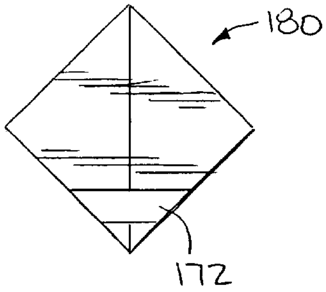
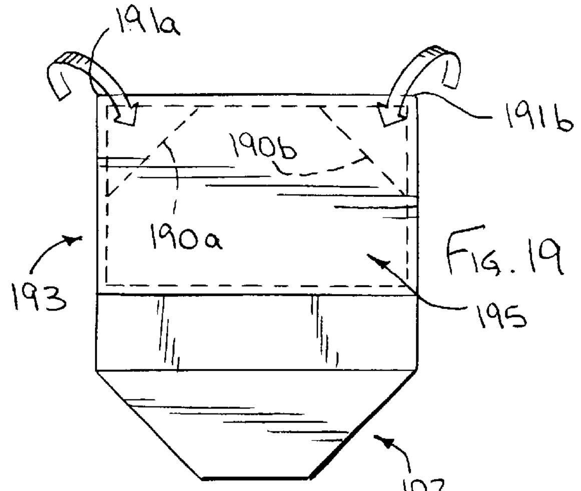
FIG. 19
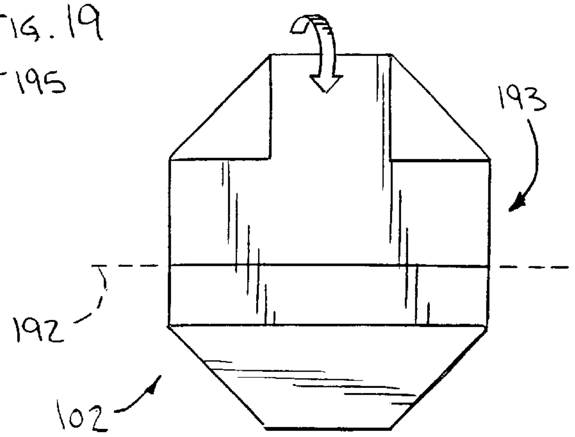
FIG 20
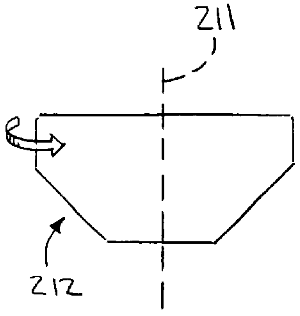
FIG. 21
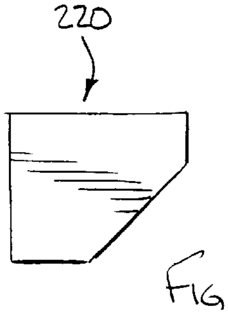
FIG. 22

PERSONAL HYGIENE PRODUCT DISPOSAL CONTAINER

FIELD OF THE INVENTION

The present invention relates to the disposal of personal hygiene products. More specifically, the invention relates to a portable product used to dispose a used sanitary article such as a sanitary napkin, incontinence pad, etc.

BACKGROUND OF THE INVENTION

Many people are faced with the challenge of disposing used sanitary articles in a discrete and efficient manner. Personal hygiene products such as incontinence pads and condoms are difficult to dispose of. Women, in particular, are faced with very personal challenges when they need to dispose of feminine products away from home. Women will often resort to wrapping the used sanitary napkin or tampon in an awkward bundle of toilet tissue. This does not provide a secure wrapping. More often than not, restrooms in restaurants, stores, and in places of work do not have convenient waste receptacles in the toilet stalls. Even when such receptacles are provided, many women choose not to use them, for health and/or safety reasons. If she is in the home of a friend, the pad cannot be flushed, and leaving it in the friend's waste container will create an unpleasant odor. In this case, she may tuck the bundle of toilet tissue into her purse to carry it until she gets home.

Methods and products to dispose of used sanitary napkins are known in the art. The most common product available is the Sanibag™, manufactured by Beier & Company, which is sometimes provided in public restrooms. The Sanibag is formed as a relatively long, rectangular bag with an open top, which provides a narrow opening for receiving the sanitary napkin. Unfortunately, the Sanibag is awkward to work with due to its design, and seals poorly. In other known products, the disposal product is directly attached to the pad itself, but this creates an undesirable bulkiness when worn.

BRIEF DESCRIPTION OF THE DRAWINGS

FIG. 17 illustrates folds lines for an alternative store position for the container of FIG. 5.

FIG. 18 is a perspective view of the container of FIG. 17 in the alternative store position.

FIGS. 19–21 illustrate progressive folding stages of the sheet of FIG. 11 as it is assembled into an alternative container similar to that of FIGS. 12–15.

FIG. 22 is a side elevation view of the container of FIGS. 19–21 folded into a store position.

DETAILED DESCRIPTION

Figure 1:
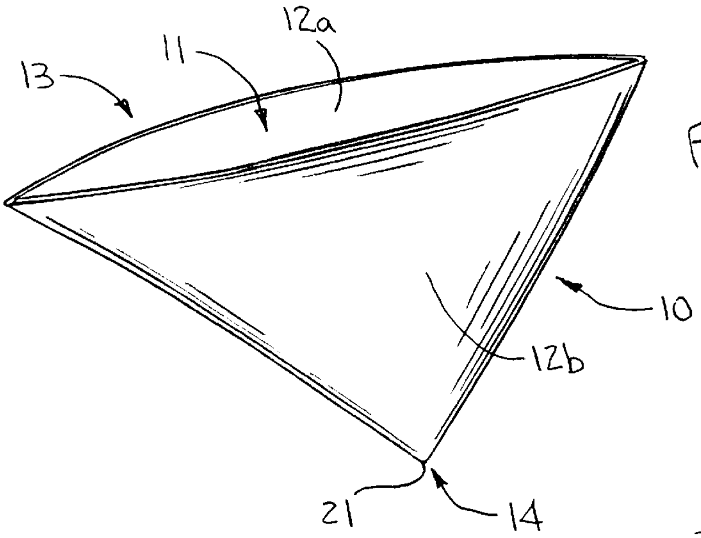
FIG. 1 is a perspective view of an assembled container constructed in accordance with the teachings of the present invention, the container being shown in a receive position.

Referring now to the drawings, the assembled container 10 is shown in FIG. 1 in the receive position, whereby the container 10 is in position to accept a used napkin. The container 10 has two opposing sheets, 12*a* and 12*b*. Container 10 is further defined by the receptacle end 13 and base end 14. The receptacle end 13 has a relatively large opening mouth 11. On the base end 14, there is a bottom point 21.

Figure 2:
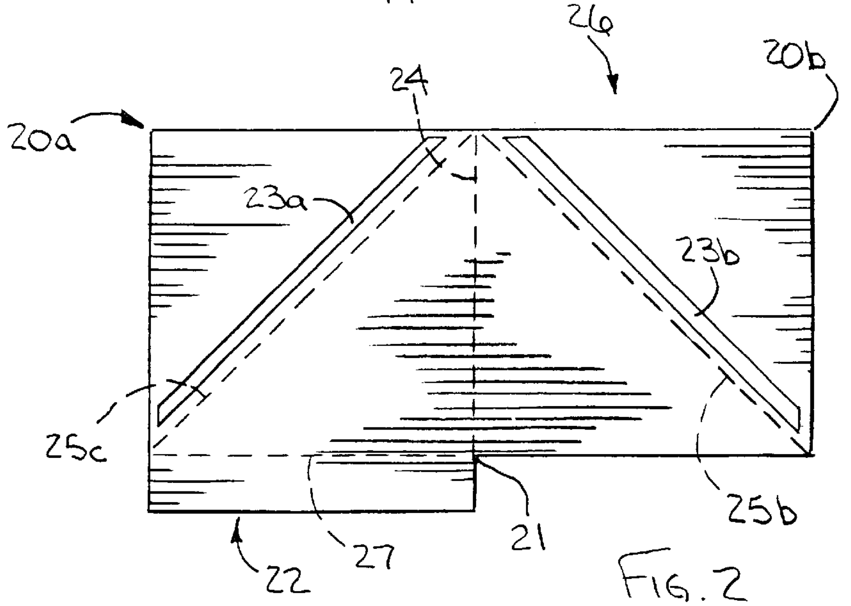
FIG. 2 is a plan view of a sheet used to form the container, the sheet being shown prior to assembly.

FIG. 2 shows the layout of a sheet 26 prior to assembly of the container 10. The sheet 26 can be made of anything that will fold easily and maintain a crease. Furthermore, this sheet 26 may be formed of or coated with a material that is resistant to the seepage of liquid. For example, the sheet 26 may be provided as paper treated with water-resistant material. The sheet 26 is generally rectangular in shape, and a tab 22 extends for approximately one half the length of the longer side of the rectangle. As is shown in FIG. 2, the sheet 26 may have a length that is twice as long as its width.

Seal strips 23*a* and 23*b* may be affixed to the sheet. These seal strips 23*a* and 23*b* can be formed of any releaseable sealant known in the art. These seal strips serve to seal the container 10 shut when it is completely assembled as shown in FIG. 1 and in use.

Figure 3:
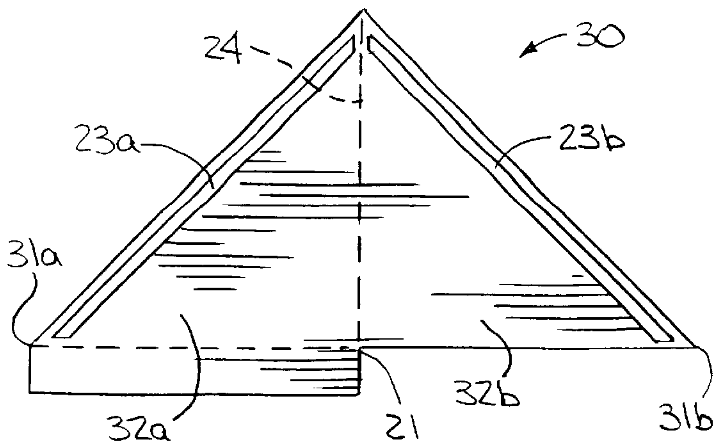
FIGS. 3–8 illustrate progressive folding stages of the sheet of FIG. 2 as it is assembled into the container and the store position.

The dashed lines 24, 25*a*, 25*b*, and 27 of FIG. 2 represent fold lines in the sheet 26. To first make the container 10, corner points 20*a* and 20*b* are folded along fold lines 25*a* and 25*b* such that both corner points 20*a* and 20*b* meet at bottom point 21. At this point, the sheet 26 has been folded into an intermediate product 30. The intermediate product 30 resembles an isosceles triangle, as shown in FIG. 3, and is defined by two panels, 32*a* and 32*b*, and fold line 24 is an axis running along the centerline of intermediate product 30.

Figure 4:
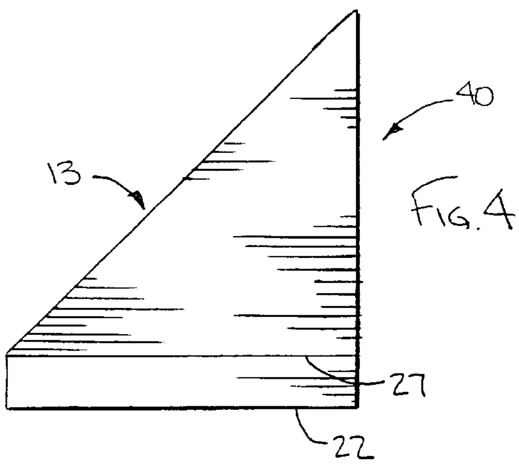

Next, the bottom corner points 31*a* and 31*b* are folded toward each other along the fold line 24. At this point the seal strips 23*a* and 23*b* may meet and create a seal at the mouth opening 11. The sheet 26 now resembles a right triangle 40, as shown in FIG. 4. The tab 22 is folded along fold line 27 (also seen in FIG. 2) until it is contiguous with the body of right triangle 40. The tab 22 is then affixed to the body of the right triangle 40 to create a water resistant seal. The seal can be formed using any of the well-known sealants, glues or tapes.

Figure 5:
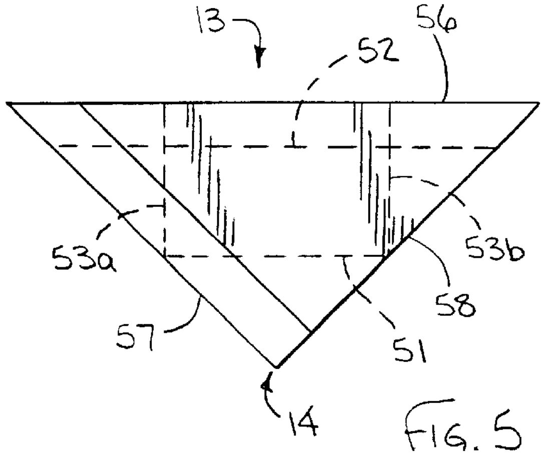

At this point, the container 10 is now formed from the sheet 26 and is in the receive position, as best shown in FIGS. 1 and 5. The container 10 includes two opposing sheets 12*a* and 12*b*, which meet at a first edge 57, a second edge 58, and a third edge 56. The sheets 12*a* and 12*b* are secured together along the first edge 57 and the second edge 58. Along the third edge 56 the opposing sheets 12*a* and 12*b* are not secured together, allowing mouth opening 11 to be formed.

The container 10 may be opened to receive a used sanitary napkin, tampon, condom, or other personal item. The container is opened by pulling apart the opposing sheets 12*a* and

12*b* at the receptacle end 13. This breaks the seal between sealants 23*a* and 23*b*, to open the container and provide a large mouth opening 11. A user can then place the used sanitary article inside the container 10 and then reseal the container 10 by pressing the opposing sheets back together at the mouth area 11, thereby re-engaging the sealant 23*a* and 23*b*.

It is also well within the scope of this invention for a container formed by two opposing sheets, with two edges permanently secured, with the third edge releasably secured, to be assembled in several different ways. This includes, but is not limited to, securing two common triangular sheets of paper together along two edges, or folding a triangular sheet of paper in half to form two similar opposing triangular sheets, then securing along one edge.

Figure 6:
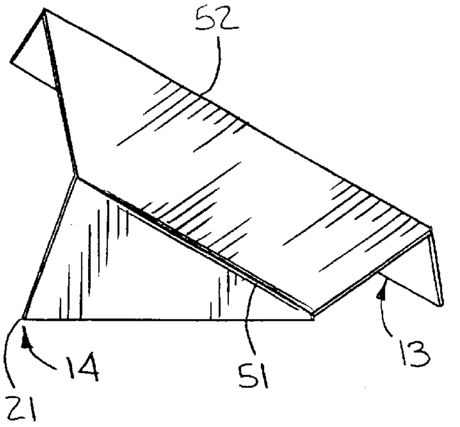

The container 10 can be further folded into a store position to occupy a smaller space. As shown in FIG. 5, a base end fold line 51 and a receptacle end fold line 52 are defined. Further, transverse fold lines 53*a* and 53*b* are shown. As shown in FIG. 6, receptacle end 13 is folded down around receptacle end fold line 52. Receptacle end fold line 52 can be selected at a distance from the mouth 11 such as to facilitate ease of handling and use. Thus the distance from receptacle end fold line 52 to mouth 11 should be long enough such that the user can grasp and easily manipulate the mouth 11 to open it. If no sealing strips 23*a* and 23*b* are used, the act of folding the mouth end closed is an effective sealing method.

Base end 14 is folded in the opposite direction, i.e. away from the downward folded mouth 11, around the base end fold line 51. Base end fold line 51 may be positioned half way from base point 21 to the receptacle end fold line 52. In this manner base point 21, when folded, will meet with roughly a midpoint of the receptacle end fold line 52.

Figure 7:
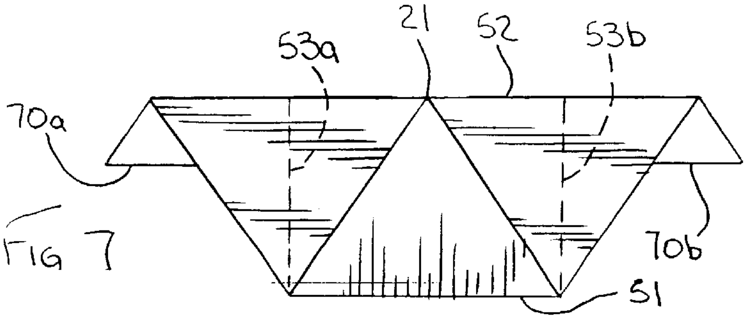

FIG. 7 shows the positions of transverse fold lines 53*a* and 53*b*. The transverse fold lines 53*a* and 53*b* are at a right angle to bottom fold 51 and the end points of the bottom fold line 51 are coincident with the bottom end points of the transverse fold lines 53*a* and 53*b*. Mouth endpoints 70*a* and 70*b* are folded inward along the transverse fold lines 53*a* and 53*b*, respectively, towards and overlapping the bottom point 21. The mouth endpoints 70*a* and 70*b* may be held to the bottom point by a fastener 72 (FIG. 8), which may be in the form of a releasable tape, a bead of releaseable glue, or other adhesive.

Figure 8:
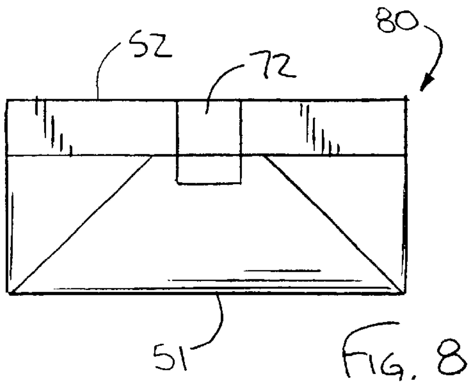
Figure 9:
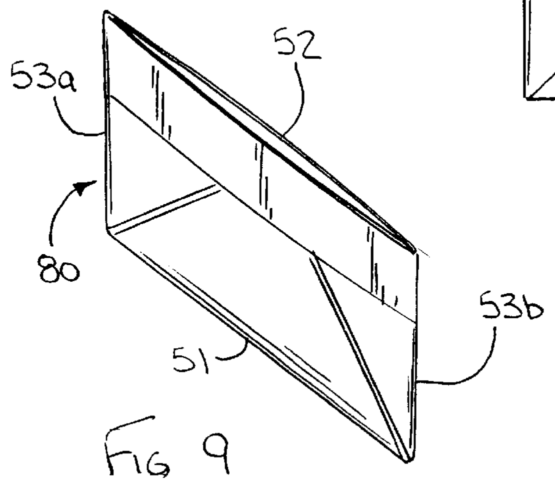
FIG. 9 is a perspective view of an assembled container in a folded store position.

FIG. 8 shows the container 10 in the fully folded store position 80. A perspective view of container 10 in the fully folded store position 80 is shown in FIG. 9. In the store position, the container 10 is transformed into a convenient, easy to carry, and compact disposal system. The user can easily seal a used pad inside the container, and put the entire package into her purse, confident that it will not leak, and dispose of it at her convenience.

A second example of folding the container 10 into a smaller store position is shown in FIGS. 17–18. A fold line 171*a* is defined by endpoints at the approximate midpoint of unsecured edge 56 and the approximate midpoint of secured edge 58. A second fold line 171*b* is defined by endpoints at the approximate midpoint of unsecured edge 56 and the approximate midpoint of secured edge 57. A strip of tape or similar adhesive is adhered to the sheet 12*a* (directly behind the sheet 12*b*).

The store position is created by folding the container 10 about the fold lines 171*a* and 171*b*, such that the mouth endpoints 70*a* and 70*b* are both folded to and meet at the bottom point 21. The strip of tape is then applied as shown in FIG. 18, and the mouth endpoints 70*a* and 70*b* are secured at the bottom point 21.

As best shown in FIG. 17, a seal strip 173 may be provided along the unsecured edge 56 for closing the container 10 once a used hygiene product has been deposited therein. The seal strip 173 may be in the form of a releasable adhesive, such as a sprayed repositional adhesive, covered by a backing strip, so that the adhesive is exposed only when needed by removing the backing strip.

Figure 10:
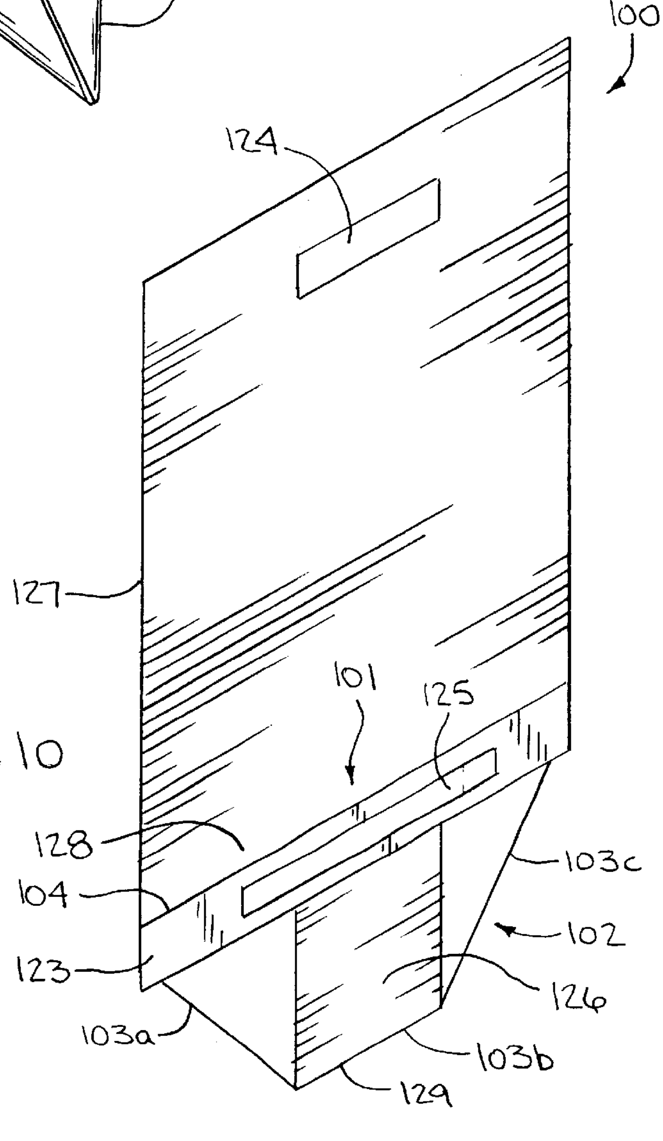
FIG. 10 is a perspective view of a second example of an assembled container constructed in accordance with the teachings of the present invention, the container being shown in a receive position.

In a second example of the container, as shown in FIG. 10, the assembled container 100 is shown in the receive position, whereby the container 100 is in position to accept a used napkin. The container 100 has a basket portion 102 defining a mouth 101. It also has a lip sealant 125 and a rear panel sealant 124. These sealants can be constructed of anything known in the art to be effective sealants or adhesives such as tape. It has a relatively wide receptacle end 128 and a relatively narrow base end 129. The container 100 has secured edges 103*a*, 103*b*, and 103*c*, and an unsecured edge 104. The container 100 has an overall hexagonal shape.

Figure 11:
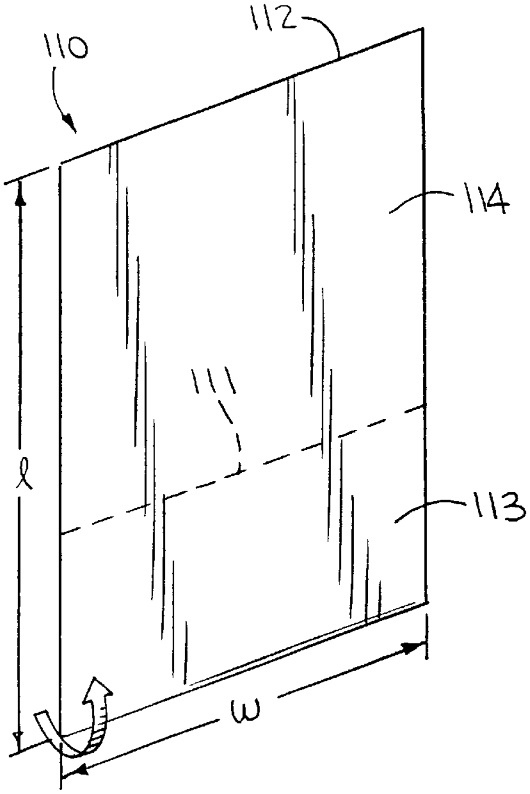
FIG. 11 is a perspective view of a sheet used to form the second example of the container, the sheet being shown prior to assembly.

FIG. 11 shows the layout of a liquid resistant sheet 110 prior to assembly of the container 100. The sheet 110 has a length l, a width w, and a top edge 112. In the first step, the sheet 110 is folded about first folding axis 111, with the bottom panel 113 folded up contiguous against the top panel 114 of the sheet. The first folding axis 111 can be located anywhere along the length l, so long as the distance from the first folding axis 111 to the top edge 112 is greater than one half the width w. In the present example the first folding axis is located approximately ⅔ of the length l from the top edge 112. Referring back to FIG. 10, the top panel 114 and the bottom panel 113 define two opposing panels, front panel 126 and rear panel 127 of the container 100.

Figure 12:
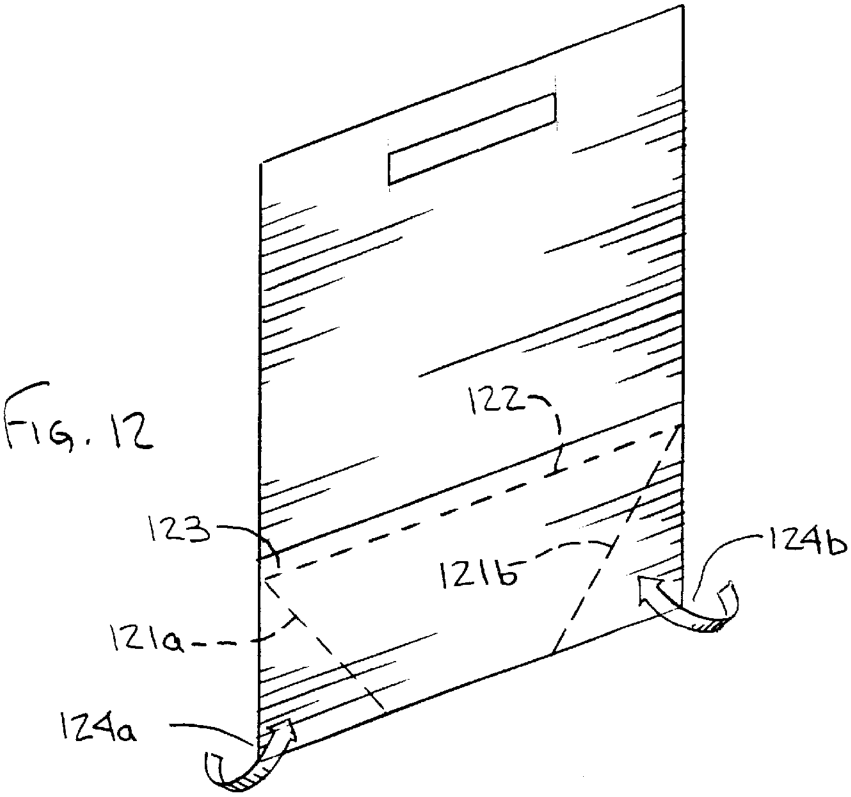
FIGS. 12–15 illustrate progressive folding stages of the sheet of FIG. 11 as it is assembled into the container and a store position.

Once the first fold has been created, the sheet 110 resembles the layout in FIG. 12. Bottom corner fold lines 121*a* and 121*b* and lip fold line 122 are then defined. Although the bottom corner fold lines 121*a* and 121*b* can be chosen to lie at any angle, an approximately 45° angle is shown. Once the bottom corners 124*a* and 124*b* are folded about the bottom fold lines 121*a* and 121*b* contiguous against the front panel 126, there remains a lip area 123. The lip fold line 122 is most advantageously chosen to have common endpoints with the bottom corner fold lines 121*a* and 121*b* as shown in FIG. 12. The lip area 123 is folded down around the lip fold line 122 contiguous with front panel 126.

At this point the container 100 is formed from the sheet 110 and is in the receive position, as best shown in FIG. 10. The secured edges 103*a*, 103*b*, and 103*c* are common edges of the front panel 126 and rear panel 127. The unsecured edge 104 is an edge of the front panel 126 which is contiguous with the body of the rear panel 127. The container 100 may be used to receive a used sanitary napkin. The front panel 126 is pulled away from the rear panel 127 to provide a mouth 101. The user can then place the used sanitary napkin in the container 100.

Figure 13:
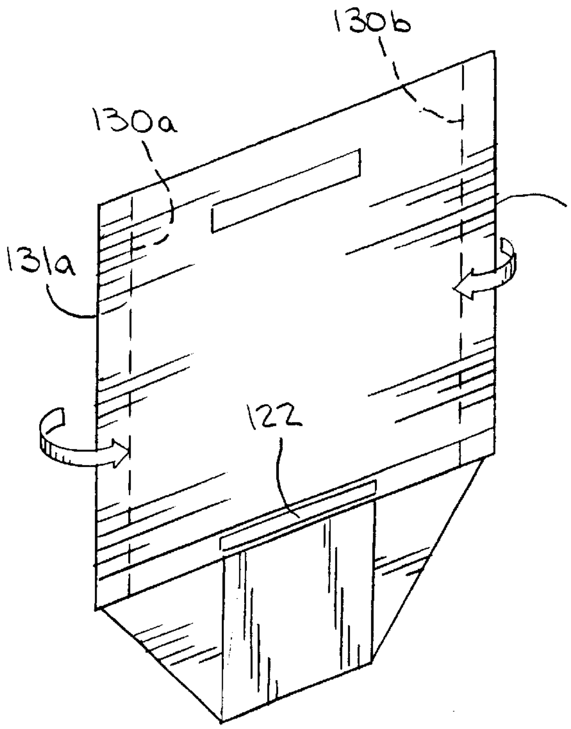
Figure 16:
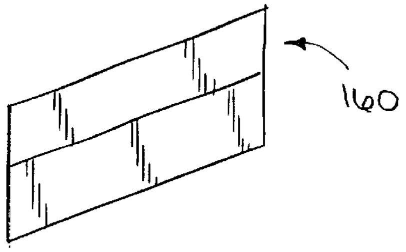
FIG. 16 is a perspective view of an assembled container in a folded store position.

The user can then fold the container 100 into a store position 160 thereby sealing the container 100 (FIG. 16). Folding will also cause the container 100 to occupy a smaller volume of space for easy transport. The side fold lines 130*a* and 130*b* of FIG. 13 are chosen such that they don't excessively lessen the volume the container 100 is able to store, yet are chosen minimize the volume the container 100 occupies while in the store position 160. The side edges 131*a* and 131*b* are folded inwards about the side fold lines 130*a* and 130*b* contiguous with the rear panel 127.

Figure 14:
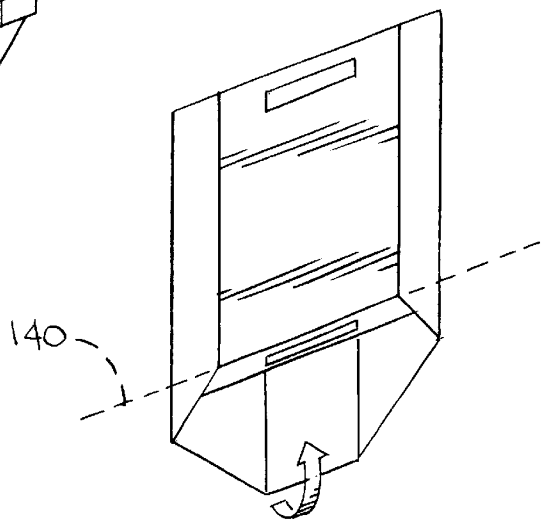

The fold line 140 of FIG. 14 is chosen to be coincident with the receptacle end 128 of the container 100. The container 100 is folded about the fold line 140 such that the basket 102 is contiguous with the rear panel 127. This will engage the lip sealant 125 against the rear panel 127 and effectively seal the basket 102.

Figure 15:
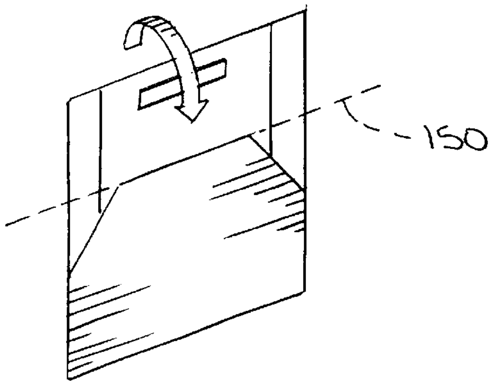

The remaining portion of the rear panel 127 not covered by the basket 102 is then folded down over the basket 102 (FIG. 15). The fold line 150 is coincident with the base end 129 of the container 100. The rear panel sealant 124 is then affixed to the basket 102. The container 100 has now been fully folded into the store position 160 as depicted in FIG. 16. Again, the container 100 is transformed into a convenient, easy to carry, and compact disposal system. The fold lines 130*a*, 130*b*, 140, and 150 may be pre-formed in the container 100 to facilitate folding of the container 100 into the store position.

The container 100 can further be placed in alternative store positions, as shown in FIGS. 19–24. Two fold lines 190*a* and 190*b* are chosen such that when the upper corner points 191*a* and 191*b* are folded about the fold lines 190*a* and 190*b*, the upper sheet portion 193 is the mirror image of the basket portion 102. The upper sheet portion 193 is then folded about a fold line 192 such that an intermediate position 212 is formed. The intermediate position 212 can then be folded into yet a smaller position, if so desired. The intermediate position 212 can be folded in half about a fold line 211 as shown in FIG. 21. The container 100 is then folded into second store position 220. It can be secured by any method known in the art such as a strip of tape.

Figure 23:
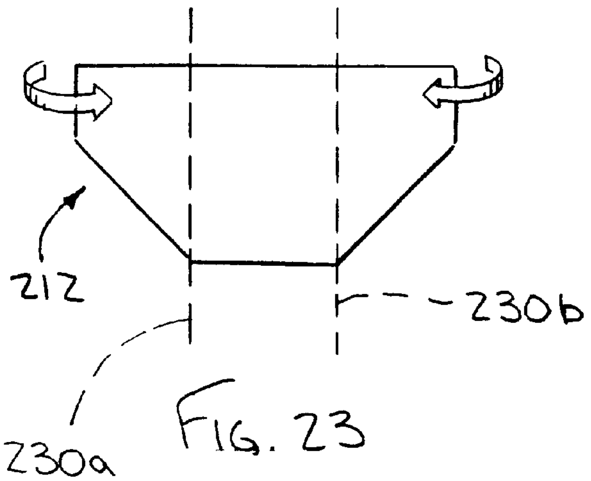
FIGS. 23–24 are side elevation views of the container of FIGS. 19–21 illustrating folding steps for an alternative store position.
Figure 24:
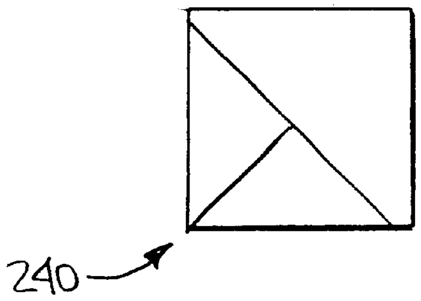

The intermediate position 212 can be folded into a thirds about fold lines 230*a* and 230*b*, as shown in FIG. 23. A third store position 240 results. Again, the third store position can be secured by any means known, including a strip of decorative tape.

As best shown in FIG. 20, the entire upper sheet portion 193 may be coated with an adhesive to form a seal portion 195. The seal portion 195 may be used to secure the container over the basket 102 after an article has been deposited therein. The seal portion 195 may be covered by a backing sheet so that the adhesive is exposed only when needed by removing the backing sheet.

The container can be enhanced in several different way. A deodorizing element 200 (See FIG. 10) can be added in the form of a pad, powder, or any other products known in the art to deodorize and/or kill bacteria in a small confined area. The container can be enhanced by adding an absorbent material 202 such as cotton. The container can further be enhanced by creating using many different colors and prints of the sheet. Still further, it will be understood that the product may be provided in a variety of sizes suitable for disposing various personal hygiene products, including diapers, incontinence pads, or condoms. Furthermore, the disposal product may be sized to enclose a plurality of hygiene products. Still further, the container may be formed with additional folds, particularly when provided in larger sizes, to decrease the size of the container when in the store position, thereby increasing the portability of the container.

As best shown in FIG. 20, the entire upper sheet portion 193 may be coated with an adhesive to form a seal portion 195. The seal portion 195 may be used to secure the container over the basket 102 after an article has been deposited therein. The seal portion 195 may be covered by a backing sheet so that the adhesive is exposed only when needed by removing the backing sheet.

The foregoing detailed description has been given for clearness of understanding only, and no unnecessary limitations should be understood therefrom, as modifications will be obvious to those skilled in the art.

What is claimed is:

1. A sanitary article disposal product comprising:

a liquid resistant sheet folded into water resistant container having first and second opposing panels of the sheet;

a relatively wide receptacle end; and a relatively narrow base end;

wherein the container may be placed in a receive condition by pulling apart the sheet panels at the receptacle end to form a mouth opening;

wherein the container includes a basket portion; and wherein side edges of the first panel of the container are folded inwards contiguous with the first panel, the basket is folded up contiguous with the first panel, and a remaining portion of the first panel not covered by the basket is folded down contiguous with the basket, thereby to fold the container in to a store position.

2. The product of claim 1, further comprising a seal strip for sealing the receptacle end.

3. The product of claim 1, in which the container is generally triangular in shape.

4. The product of claim 1, further comprising a deodorizing element inside the container.

5. The product of claim 1, wherein the container is generally hexagonal in shape.

6. The product of claim 1, in which the endpoints of the mouth opening are securedly folded to the base end, thereby to form a store position.

7. The product of claim 1, further comprising an absorbent material in the container.

8. A sanitary item disposal container comprising:

a rear sheet panel;

a front sheet panel smaller in size than the rear sheet panel and secured to the rear sheet panel along all common edges, the front sheet panel having a single unsecured edge which is contiguous with the body of the rear sheet panel;

a receptacle end being defined along the single unsecured edge of the front sheet panel; and a base end opposite the receptacle end;

wherein the container may be placed in a receive position by pulling apart the sheet panels at the receptacle end to form a mouth opening;

wherein the front panel and the rear panel form a basket portion; and wherein upper corners of an upper portion of the rear panel are folded contiguous against the rear panel, such that the upper portion mirror the basket portion, and the upper portion is folded contiguous against the basket portion, thereby forming an intermediate position.

9. The container of claim 8, wherein the intermediate position is folded in half, thereby forming a store position.

10. The container of claim 8, wherein the intermediate position is folded in thirds, thereby forming a store position.

11. The container of claim 8, further comprising a deodorizing element inside the container.

12. A method of assembling a feminine hygiene article disposal product, comprising:

providing a sheet of liquid resistant material, having a width and a length, folding the sheet about itself along a first fold axis parallel to its width, thereby creating a front panel and a rear panel, the front panel being contiguous to the rear panel, the front panel having bottom corners along the first fold axis;

folding the bottom corners inward at an angle to the first fold axis, contiguous to the front panel;

folding a portion of the front panel down contiguous with the bottom corners.

13. A method of assembling a feminine hygiene article disposal product, comprising:

providing a sheet of liquid resistant material, having a width and a length, folding the sheet about itself along a first fold axis parallel to its width, thereby creating a front panel and a rear panel, the front panel being contiguous to the rear panel, the front panel having bottom corners along the first fold axis and defining a top portion and a middle portion;

folding the bottom corners inward at an angle to the first fold axis, contiguous to the front panel; and folding the top portion of the front panel down over at least a part of the middle portion.

14. The method of claim 13, further comprising folding the rear panel down contiguous with the front panel.

15. The method of claim 13, further comprising disposing a liquid absorbent material between the front panel and the rear panel.

* * * * *